(12) United States Patent
Yonezawa

(10) Patent No.: US 10,176,614 B2
(45) Date of Patent: Jan. 8, 2019

(54) IMAGE PROCESSING DEVICE, IMAGE PROCESSING METHOD, AND PROGRAM

(71) Applicant: CANON KABUSHIKI KAISHA, Tokyo (JP)

(72) Inventor: Keiko Yonezawa, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 85 days.

(21) Appl. No.: 15/372,243

(22) Filed: Dec. 7, 2016

(65) Prior Publication Data
US 2017/0169596 A1    Jun. 15, 2017

(30) Foreign Application Priority Data
Dec. 10, 2015 (JP) .................. 2015-241565

(51) Int. Cl.
| | |
|---|---|
| G06T 11/60 | (2006.01) |
| H04N 5/232 | (2006.01) |
| G06T 7/00 | (2017.01) |
| A61B 3/00 | (2006.01) |
| A61B 3/12 | (2006.01) |
| G06T 5/50 | (2006.01) |
| G06T 7/30 | (2017.01) |
| G06K 9/00 | (2006.01) |

(52) U.S. Cl.
CPC ............ *G06T 11/60* (2013.01); *A61B 3/0025* (2013.01); *A61B 3/1225* (2013.01); *G06T 5/50* (2013.01); *G06T 7/0012* (2013.01); *G06T 7/30* (2017.01); *H04N 5/23293* (2013.01); *G06K 9/0061* (2013.01); *G06T 2207/10016* (2013.01); *G06T 2207/20221* (2013.01); *G06T 2207/30041* (2013.01)

(58) Field of Classification Search
CPC ........... A61B 3/12; A61B 3/0025; A61B 3/14; A61B 3/0058
See application file for complete search history.

(56) References Cited

U.S. PATENT DOCUMENTS

| | | | | |
|---|---|---|---|---|
| 9,161,686 B2 * | 10/2015 | Yonezawa | ............ | A61B 3/0025 |
| 9,619,874 B2 * | 4/2017 | Yonezawa | ............ | A61B 3/0025 |
| 2009/0190092 A1* | 7/2009 | Tsukada | ................ | A61B 3/102 |
| | | | | 351/208 |
| 2012/0057127 A1* | 3/2012 | Iwase | ................... | A61B 3/0025 |
| | | | | 351/206 |
| 2012/0249957 A1 | 10/2012 | Shibata | | |

(Continued)

FOREIGN PATENT DOCUMENTS

JP      2007-252692 A      10/2007

*Primary Examiner* — Bobbak Safaipour
(74) *Attorney, Agent, or Firm* — Canon U.S.A., Inc. IP Division

(57) ABSTRACT

A registration unit configured to perform first registration of the first image (WF-SLO image) and the second image (AI-SLO image) included in the same set and second registration of the first images included in the different sets and to generate positional information of these registration; and a superimposition unit configured to superimpose the second image included in a first set and the second image included in a second set that is the set acquired after the first set on the first image included in the first set or on the first image included in the second set based on the positional information generated by the registerer to generate a superimposed image are provided.

17 Claims, 8 Drawing Sheets

(56) References Cited

U.S. PATENT DOCUMENTS

| | | | |
|---|---|---|---|
| 2014/0185889 A1* | 7/2014 | Yonezawa | A61B 3/0025 382/128 |
| 2015/0272432 A1* | 10/2015 | Satake | A61B 3/0025 351/206 |
| 2015/0272434 A1* | 10/2015 | Satake | A61B 3/0058 351/206 |
| 2015/0339822 A1 | 11/2015 | Onda | |
| 2016/0012575 A1* | 1/2016 | Yonezawa | A61B 3/0025 348/78 |
| 2016/0143529 A1* | 5/2016 | Miyashita | A61B 3/152 351/208 |
| 2017/0181624 A1* | 6/2017 | Biernat | A61B 3/0058 |

* cited by examiner

IMAGE PROCESSING DEVICE, IMAGE PROCESSING METHOD, AND PROGRAM

BACKGROUND

Technical Field

The present disclosure relates to an image processing device and an image processing method for processing images of an eye fundus of a subject eye taken along a time course and relates to a program for causing a computer to execute the image processing method.

Description of the Related Art

In a visual function which is assumed to be an important function among five senses of humans, photoreceptor cells of the retina positioned at an eye fundus of a subject eye plays an important role. Recently, techniques of taking images of the retina at the eye fundus with high definition have been established using an aberration correction (compensation) technique, and finding of new knowledge and establishment of diagnostic values about the visual function are expected.

An adaptive optics scanning laser ophthalmoscope (hereinafter, referred to as "AO-SLO") apparatus is an ophthalmoscope which applies the techniques of telescopes of acquiring clear star images by compensating for fluctuations in air to image-taking of eyes. This AO-SLO apparatus enabled resolving of each one of the photoreceptor cells of the retina of the subject eye. It is said that, in the vicinity of the fovea centralis (fovea) where the photoreceptor cells have a highest density, the photoreceptor cells are present at an interval of about 2 μm. Today, in order to draw up to the photoreceptor cells of the fovea centralis, development for improving the resolution is being continued.

In order to lead to clinical values of the taken images of the photoreceptor cells, the techniques capable of observing the photoreceptor cells in the same region of the eye fundus along a time course and quantitatively analyzing changes thereof are required. In many cases, the images taken by the AO-SLO apparatus (hereinafter, referred to as "AO-SLO images") have small view angles (image-taking ranges are small) since the resolutions thereof are high. Therefore, in order to perform time-course comparison of images, first, a plurality of AO-SLO images taking the same region have to be acquired, and, furthermore, fine registration has to be performed between the acquired images. As a conventional technique about this, for example, there is a technique of Japanese Patent Laid-Open No. 2007-252692.

Specifically, Japanese Patent Laid-Open No. 2007-252692 discloses the techniques in which, in order to perform time-course comparison between tomographic images of the retina by OCT (Optical Coherence Tomography), surface images (eye-fundus images) of the eye fundus are acquired at the same time as the tomographic images; then, first, the surface images are registered with each other; and, then, the tomographic images associated with the surface images are registered with each other to perform comparison.

However, in the techniques disclosed in Japanese Patent Laid-Open No. 2007-252692, since the surface images to be registered have to be specified first, the comparison of the small-view-angle surface images of the eye fundus of the subject eye cannot be efficiently performed.

Accordingly, there is a need to provide a mechanism capable of efficiently performing the comparison of small-view-angle surface images of the eye fundus of the subject eye.

SUMMARY

An image processing device of the present disclosure has: an image acquirer configured to acquire first images and second images included in a first and a second sets, wherein each of the first and the second sets includes at least one of the first images obtained by imaging a first region having a predetermined size at an eye fundus of a subject eye and the second images obtained by imaging a second region that is smaller the predetermined size, and wherein the first and the second images included in the same set are associated with each other based on an imaging period; a registerer configured to perform first registration of the first image and the second images included in the same set and second registration of the first images included in the different sets and to generate positional information of the first registration and the second registration; and a superimposer configured to superimpose the second images included in the first set and the second images included in the second set acquired after the first set on one of the first images included in the first set or one of the first images included in the second set based on the positional information generated by the registerer to generate a superimposed image.

Further features of the present disclosure will become apparent from the following description of exemplary embodiments (with reference to the attached drawings).

DESCRIPTION OF THE EMBODIMENTS

Hereinafter, modes (embodiments) for carrying out the present disclosure will be described with reference drawings.

(First Embodiment)

First, a first embodiment of the present disclosure will be described.

In the first embodiment, a method of acquiring images of the retina positioned at an eye fundus of a subject eye taken along a time course by an image-taking device and then perform registration between two or more images of the same region. Specifically, AO-SLO images are registered with a wide-view-angle SLO image (hereinafter, referred to as "WF-SLO image") acquired as the same set (for example, taken on the same day). Furthermore, registration of each of the images included in a plurality of different sets (for example, sets acquired on different days) is performed. Then, based on the positional information of these images, the AO-SLO images acquired as the different sets (for example, taken on different days) are superimposed on a single WF-SLO image among the WF-SLO images acquired as the different sets to generate a superimposed image.

Then, in the first embodiment, when an evaluation region is selected in the superimposed image as a region to be subjected to analysis, all the AO-SLO images including the evaluation region are displayed. Then, when the images to be subjected to fine comparison are selected from among the displayed AO-SLO images, registration at higher accuracy is performed between the selected images.

In this manner, in the first embodiment, time-course comparison at the eye fundus of the subject eye can be efficiently performed by generating the superimposed image by superimposing the AO-SLO images acquired as the different sets (acquired in different periods) onto the single WF-SLO image. Moreover, the evaluation region can be selected in the superimposed image, and, as a result, the image desired to be compared can be efficiently selected. Furthermore, errors in registration processing can be reduced by performing fine registration only for the images including the evaluation region.

[Schematic Configuration of Ophthalmic Apparatus]

Figure 1:
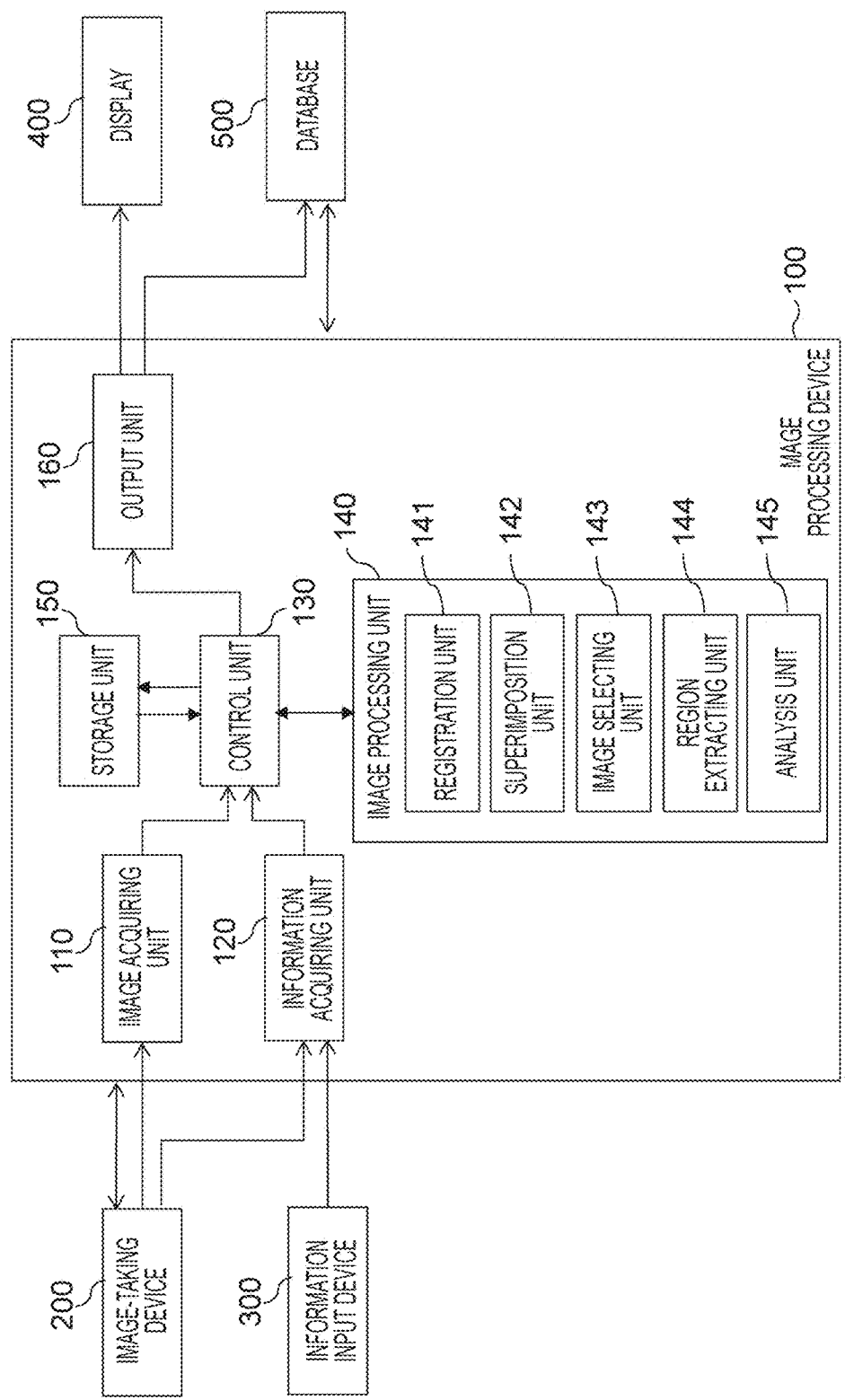
FIG. 1 is a block diagram showing an example of a schematic configuration of an ophthalmic apparatus including an image processing device according to a first embodiment of the present disclosure.

FIG. 1 is a block diagram showing an example of a schematic configuration of an ophthalmic apparatus 10 including an image processing device 100 according to the first embodiment of the present disclosure.

As shown in FIG. 1, the ophthalmic apparatus 10 according to the present embodiment is formed by having an image processing device 100, an image-taking device (for example, AO-SLO device) 200, an information input device 300, a display 400, and a database 500.

The image-taking device 200 is a device which takes images of a retina positioned at an eye fundus of a subject eye and generates planar images such as AO-SLO images, wide-view-angle WF-SLO images, etc. Herein, the WF-SLO image corresponds to a first image obtained by taking an image of a region having a predetermined size in the eye fundus of the subject eye. Meanwhile, the AO-SLO image corresponds to a second image obtained by taking an image of a region which is in the eye fundus of the subject eye and is narrower than the above described region having the predetermined size.

The information input device 300 is a device which inputs various information to the image processing device 100.

The image processing device 100 is a device which subjects the planar images such as AO-SLO images and WF-SLO images, which are obtained by taking images of the retina positioned at the eye fundus of the subject eye by the image-taking device 200, to image processing. As shown in FIG. 1, the image processing device 100 is formed by having an image acquiring unit 110, an information acquiring unit 120, a control unit 130, an image processing unit 140, a storage unit 150, and an output unit 160.

The image acquiring unit 110 performs processing of acquiring the planar images such as the AO-SLO images and the WF-SLO images obtained by taking images of the retina positioned at the eye fundus of the subject eye by the image-taking device 200. This processing includes a case in which the planar images are directly acquired from the image-taking device 200 and also includes a case in which the planar images which have been previously obtained by the image-taking device 200, have undergone image processing, and then have been saved in the database 500 are obtained from the database 500. For example, the image acquiring unit 110 acquire the WF-SLO image (first image), which is obtained by taking the image of the region having the predetermined size in the eye fundus of the subject eye, and the AO-SLO image (second image), which is obtained by taking the image of the region which is in the eye fundus of the subject eye and is the region narrower than the region having the predetermined size, in a manner that the images are associated for each set based on an image-taking period.

The information acquiring unit 120 performs processing of acquiring various information from the image-taking device 200 and the information input device 300. For example, the information acquiring unit 120 acquires information of the subject eye from the image-taking device 200 or acquires input information from the information input device 300 by an examiner. Furthermore, the information acquiring unit 120 performs processing of acquiring an evaluation region, which is a region to be subjected to time-course evaluation, from among superimposed images generated by a later-described superimposition unit 142. The information acquiring unit 120, which performs the processing of acquiring the evaluation region, forms a region acquirer.

The control unit 130 comprehensively controls operations in the image processing device 100.

The image processing unit 140 processes the planar images such as the AO-SLO images and WF-SLO images, which are acquired by the image acquiring unit 110, based on control by the control unit 130. As shown in FIG. 1, the image processing unit 140 is formed by having: a registration unit 141, the superimposition unit 142, an image selecting unit 143, a region extracting unit 144, and an analysis unit 145.

The registration unit 141 performs inter-frame registration of the AO-SLO images and the WF-SLO images acquired by the image acquiring unit 110 and registration processes between the AO-SLO images and the WF-SLO images and between the WF-SLO images and between the AO-SLO images, which have been acquired along a time course. When these various registration processes are performed, the registration unit 141 generates positional information of the various registration. For example, the registration unit 141 performs first registration which is the registration of the WF-SLO image and the AO-SLO images forming the same set and performs second registration which is the registration of the WF-SLO images included in a plurality of different sets. Then, the registration unit 141 generates positional information of the first registration and the second registration. Furthermore, the registration unit 141 further performs third registration which is fine registration between the AO-SLO images selected by the later-described image selecting unit 143 and generates positional information of the third registration.

The superimposition unit 142 performs a process of generating a superimposed image by superimposing the AO-SLO images, which have been associated by the registration unit 141, on the WF-SLO image, which serves as a reference. For example, based on the positional information generated by the registration unit 141, the superimposition unit 142 generates a superimposed image by superimposing the AO-SLO image included in a first set, which is a previously acquired set, and the AO-SLO image included in a second set, which is a set acquired after the first set, on the WF-SLO image included in the first set or on the WF-SLO image included in the second set.

The image selecting unit 143 performs processing of selecting the AO-SLO images, which are to be subjected to fine registration (detailed time-course analysis), from among the AO-SLO images including the evaluation region acquired by the information acquiring unit 120 from within the superimposed image.

The region extracting unit 144 performs a process of extracting a common region which is a region included in common (overlapped region) in the AO-SLO images subjected to the third registration, which is fine registration, by the registration unit 141.

The analysis unit 145 performs analysis processes such as photoreceptor-cell extraction of the subject eye with respect to the AO-SLO images. Furthermore, the analysis unit 145 performs analysis processes such as photoreceptor-cell extraction of the subject eye and image comparison about the common region extracted by the region extracting unit 144.

The storage unit 150 stores a program(s), various information, etc. required when the control unit 130 performs processing. Furthermore, based on control by the control unit 130, the storage unit 150 stores the planar images acquired by the image acquiring unit 110, the various information acquired by the information acquiring unit 120, the various information obtained as a result of processing by the image processing unit 140, etc.

Based on control by the control unit 130, the output unit 160 outputs the planar images acquired by the image acquiring unit 110, the various information acquired by the information acquiring unit 120, the various information obtained as a result of the processing of the image processing unit 140, etc. to the display 400 to display them and outputs them to the database 500 to save them.

The display 400 performs processing of displaying the planar images, various information, etc. output from the output unit 160.

The database 500 performs processing of saving the planar images, various images, etc. output from the output unit 160.

[Planar Images]

Figure 2:
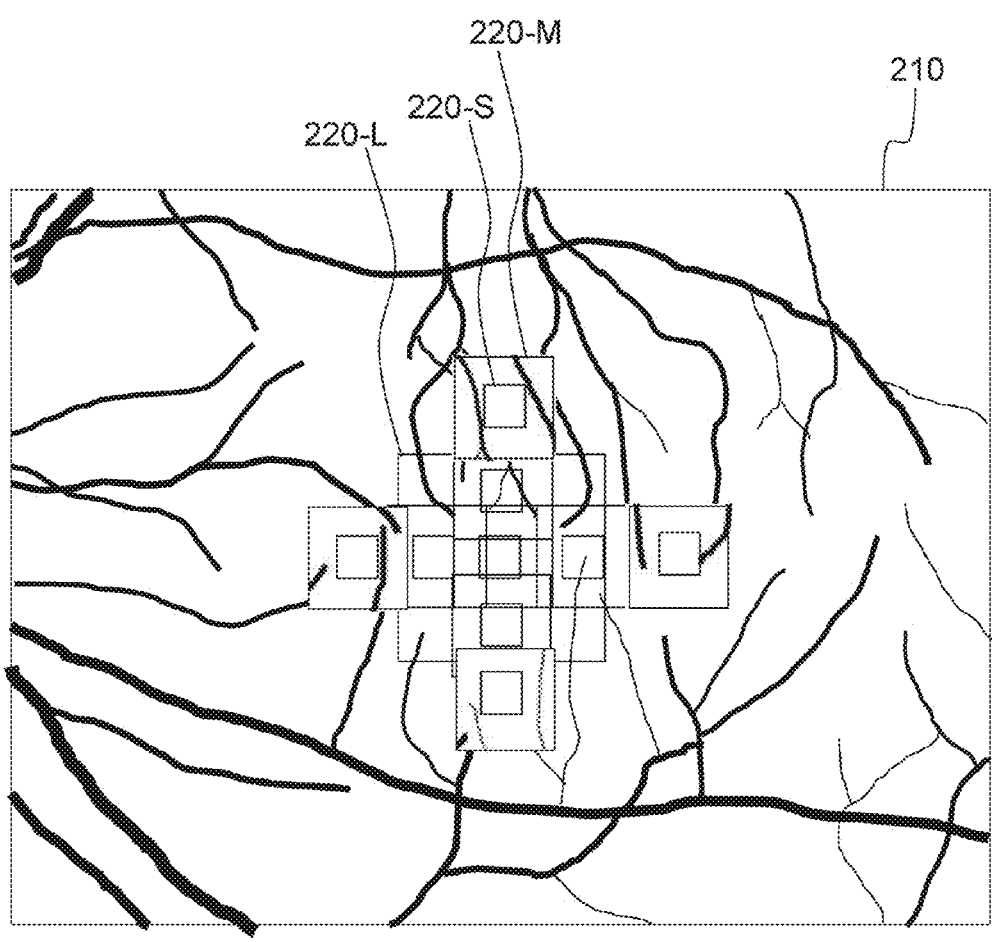
FIG. 2 is a view, according to the first embodiment of the present disclosure, schematically showing a plurality of AO-SLO images and a WF-SLO image generated by an image-taking device of FIG. 1.

FIG. 2 is a view, according to a first embodiment of the present disclosure, schematically showing a plurality of AO-SLO images and a WF-SLO image generated by the image-taking device 200 of FIG. 1. The image-taking device 200 can take images of different positions of the retina positioned at the eye fundus of the subject eye by taking images of the states in which the subject eye is staring at different positions by changing a lighting position of a fixation light.

Herein, FIG. 2 shows the wide-view-angle WF-SLO image 210 and the AO-SLO images 220 (-L, -M, -S) generated by the image-taking device 200. A set of the WF-SLO image 210 and the AO-SLO images 220 as shown in FIG. 2 is acquired by one examination. In the present embodiment, a plurality of sets each as shown in FIG. 2 are acquired by observing the same subject eye along a time course.

Figure 3:
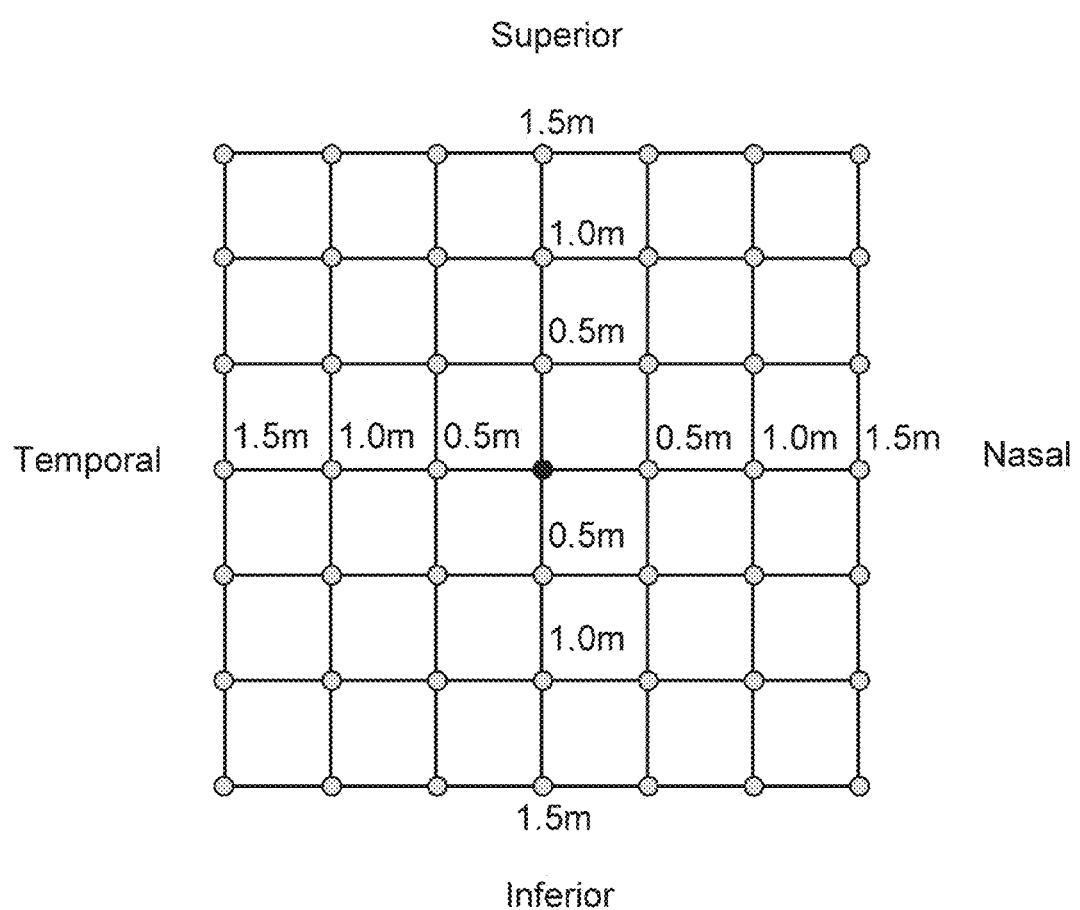
FIG. 3 is a view, according to the first embodiment of the present disclosure, showing a fixation-lamp map for operating a lighting position of a fixation lamp in the image-taking device of FIG. 1.

FIG. 3 is a view, according to the first embodiment of the present disclosure, showing a fixation-lamp map for operating the lighting position of the fixation lamp in the image-taking device 200 of FIG. 1.

First, the image-taking device 200 lights the fixation lamp in a state in which a center of the fixation-lamp map shown in FIG. 3 is selected. In this case, if an image of the subject eye staring at the presented fixation lamp is taken, the image of the vicinity of a macula of the subject eye can be taken.

Herein, the WF-SLO image 210 shown in FIG. 2 is a low-resolution wide-view-angle image acquired by an optical system different from that of the case of acquiring the AO-SLO images in the image-taking device 200 without using an adaptive optics system. The WF-SLO image 210 is an image for obtaining an overall image of the retina by taking an image of a region having a predetermined large region of the retina positioned at the eye fundus of the subject eye.

As shown in FIG. 2, when the AO-SLO images 220 having narrow view angles are registered and associated with the WF-SLO image 210, the positions where the AO-SLO images 220 having the narrow view angles are at in the entire retina of the subject eye are indicated. Hereinafter, in the present embodiment, the WF-SLO image 210 is assumed to have an image size of 8 mm×6 mm and have a pixel size of 533 pixels×400 pixels. Meanwhile, three types of resolutions are present for the AO-SLO images 220, wherein the sizes of image-taken regions are 3 types, i.e., 1.7 mm×1.7 mm, 0.82 mm×0.82 mm, and 0.34 mm×0.34 mm, and the pixel size of all of them is common and is 400 pixels×400 pixels. Herein, the AO-SLO image having the size of the image-taken region of 1.7×1.7 mm is assumed to be the AO-SLO image 220-L having a view angle L. Also, the AO-SLO image having the size of the image-taken region of 0.82 mm×0.82 mm is assumed to be the AO-SLO image 220-M having a view angle M. Also, the AO-SLO image having the size of the image-taken region of 0.34 mm×0.34 mm is assumed to be the AO-SLO image 220-S having a view angle S.

Meanwhile, the WF-SLO image 210 and the AO-SLO images 220 described herein are acquired as moving images formed by a plurality of frames, and frame rates and the number of frames, which are formed depending on image-taking time, are varied. In the present embodiment, the AO-SLO image 220 is assumed to have a frame rate of 32 frames per second, have image-taking time of 1 second, and be formed by 32 frames. Meanwhile, the WF-SLO image 210 is assumed to have a frame rate of 14 frames per second, have image-taking time of 1 second, and be formed by 14 frames. Meanwhile, in photoreceptor-cell analysis described below, the S-view-angle AO-SLO image 220-S is assumed to be an analysis target. Meanwhile, the WF-SLO image 210 and the AO-SLO images 220 are referred to as planar images.

[Image-Taking Protocol]

An image-taking protocol of the subject eye is different depending on a disease, etc. of the subject eye to be focused on. However, as a standard protocol, first, an image of the WF-SLO image 210 having the macula at the center thereof is taken, and, then, images of a plurality of positions of the retina are taken while combining the AO-SLO images 220 having different resolutions. Also, if the same subject eye is to be observed along a time course, it is general to take images by the same protocol; however, there is a case in which a plurality of images of only a periphery of a focused diseased part are taken while changing positions little by little.

[Processing Procedure of the Image Processing Device 100]

Figure 4:
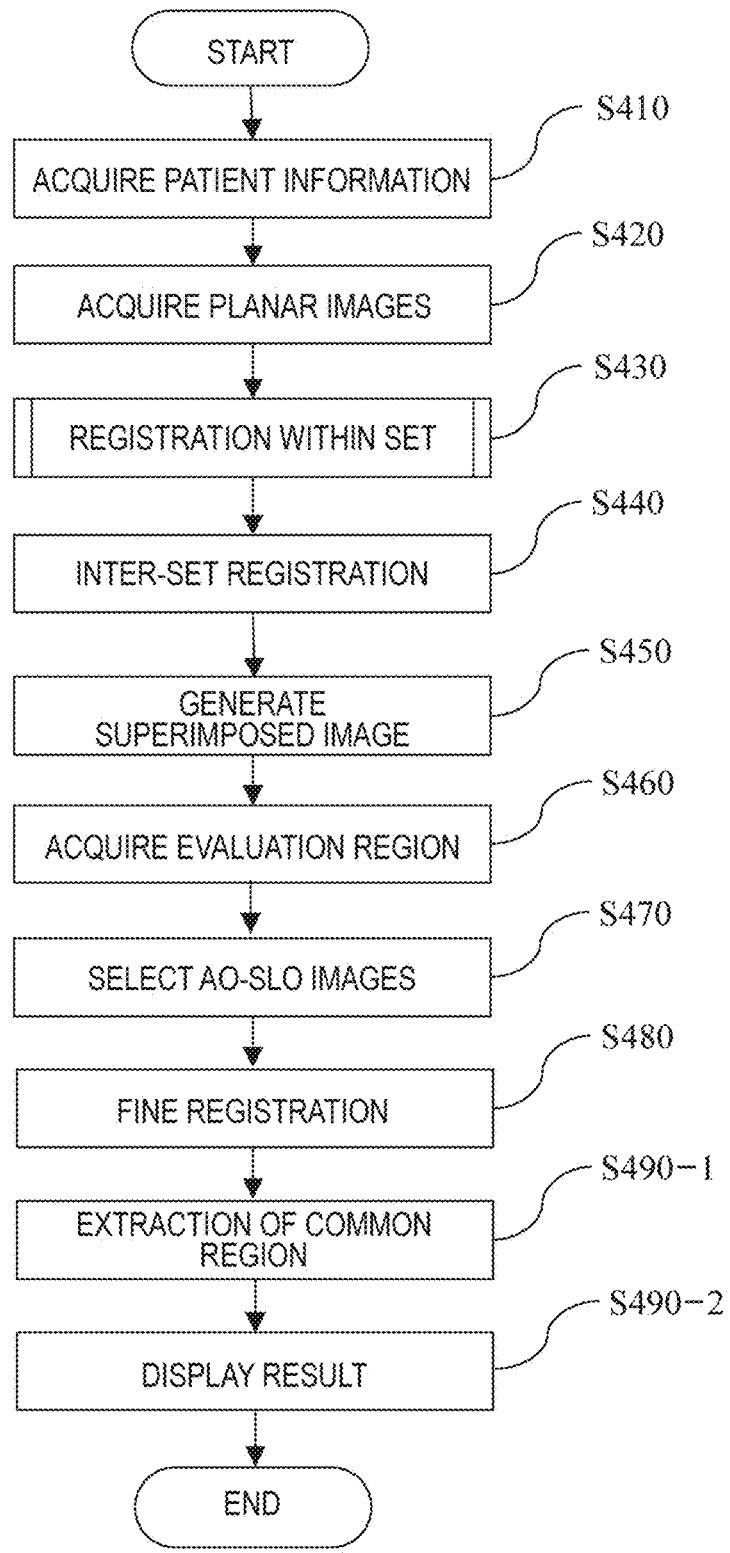
FIG. 4 is a flow chart showing an example of a processing procedure of an image processing method by the image processing device according to the first embodiment of the present disclosure.

FIG. 4 is a flow chart showing an example of a processing procedure of an image processing method by the image processing device 100 according to the first embodiment of the present disclosure.

<Step S410>

First, in step S410, the information acquiring unit 120 acquires information of a subject eye as patient information input from the information input device 300. Then, the information acquiring unit 120 stores the acquired information of the subject eye into the storage unit 150 via the control unit 130. Herein, the information of the subject eye includes examinee information such as an ID, birth date, etc. of an examinee, information of measurement data such as an eye-axis length of the subject eye, and, furthermore, information such as images taken in the past.

<Step S420>

Subsequently, in step S420, the image acquiring unit 110 acquires a plurality of sets of planar images (WF-SLO images 210 and AO-SLO images 220) acquired along a time course from the image-taking device 200 or the database 500. Then, the image acquiring unit 110 stores the acquired sets of the planar images into the storage unit 150 via the control unit 130. Herein, in the present embodiment, the set of the planar images refers to images formed by, for example, the WF-SLO images 210 and the AO-SLO images 220 taken on the same day in a case in which images of the same subject eye are taken along a time course. However, for example, in a case in which images are taken before and after treatment and subjected to comparison, the images of before and after the treatment may be treated as those of mutually different sets in some cases even if they are taken on the same day.

<Step S430>

Subsequently, in step S430, the registration unit 141 performs registration of the WF-SLO image 210 and the AO-SLO images 220, which are included in the same set, with respect to each set of the sets of the planar images acquired in step S420. In this process, the registration unit 141 generates positional information of registration of each set. The registration within the set in this step S430 corresponds to first registration, and detailed processes of this step S430 will be described below by using FIG. 5.

Figure 5:
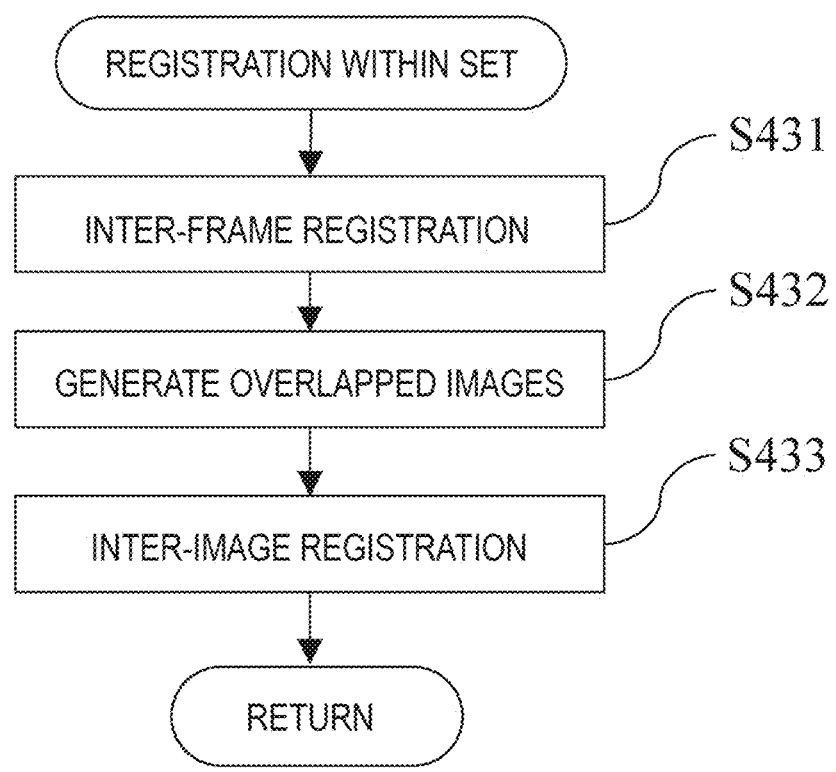
FIG. 5 is a flow chart showing an example of a detailed processing procedure of a registration process within a set in step S430 of FIG. 4.

FIG. 5 is a flow chart showing an example of a detailed processing procedure of the registration within a set in step S430 of FIG. 4.

<<Step S431>>

First, in step S431, the registration unit 141 performs inter-frame registration of the AO-SLO image or the WF-SLO image. As described above, the AO-SLO image is formed by 32 images (frames), and the WF-SLO image is formed by 14 images (frames). These images are taken at the same position on the retina of the subject eye, however, positional gaps or distortion within the images are generated due to small involuntary eye movement of the subject eye. Therefore, the distortion and positional gaps have to be corrected by performing inter-frame registration. Such positional gaps and distortion within the frame have larger influence on the AO-SLO image, which has a small image-taking range, compared with the WF-SLO image, which has taken a large range. Therefore, a processing procedure about the case of the AO-SLO image will be described.

First, the frame having the smallest distortion is selected from among the 32 frames and employed as a reference frame. Then, registration of the other frames is performed with respect to the reference frame. This selection of the reference frame can be performed by a user or can be automatically performed by using an image-quality index, etc. A plurality of methods are known as the method of registering the other frames with the reference frame. However, herein, registration using a phase-only correlation method is used. This is for a reason that, since the AO-SLO image, which has taken an image of the retina, does not include a characteristic object(s) serving as a mark within the image in many cases, a method capable of performing highly-accurate registration even with the distribution information of photoreceptor cells is required.

Specifically, the registration unit 141 selects one frame which is not the reference frame (hereinafter, the selected frame will be referred to as "current-frame") and calculates parallel moving amounts for the entirety of the reference frame and the current-frame by using the phase-only correlation method. Then, the registration unit 141 obtains a region in which the reference frame and the current-frame are overlapped in the parallelly moved state and sets a plurality of small regions in the region. Herein, the registration unit 141 sets the 6 small regions, each of which has 64 pixels×64 pixels, vertically and horizontally, respectively, i.e., sets 36 small regions in total. Then, the registration unit 141 obtains positional gaps (parallel moving amounts) between the small regions by using the phase-only correlation method again with respect to images included in the reference frame and the current-frame corresponding to the small regions. Then, the registration unit 141 obtains affine transformations, which optimize the parallel movements at the 36 locations, and adapt them to the current-frame. Furthermore, if there are deformation of the small regions obtained by the affine transformations and are differences in the parallel moving amounts obtained in the above description, the registration unit 141 also performs fine correction thereof and generates an image which has undergone correction of the position based on the obtained information. Then, the registration unit 141 performs the above described process with respect to all of the 31 frames excluding the reference frame, thereby acquiring the AO-SLO image which has been registered with the reference frame (hereinafter, referred to as "registered AO-SLO image"). Furthermore, also regarding the WF-SLO image, the registration unit 141 acquires a registered WF-SLO image by a method similar to that of AO-SLO.

<<Step S432>>

Subsequently, in step S432, the registration unit 141 generates an overlapped image using the registered AO-SLO image (hereinafter, referred to as "overlapped AO-SLO image"). Specifically, with respect to the pixels (400 pixels× 400 pixels) of the reference frame, the registration unit 141 accumulates pixel values of the corresponding frames and acquires average values thereof. Herein, the registration unit 141 obtains the average values only by the pixels having the corresponding pixel values since there is a frame(s) in which the corresponding pixel is not present with respect to a certain pixel due to a positional gap. Moreover, also regarding the WF-SLO image, the registration unit 141 generates an overlapped WF-SLO image by a method similar to that of the AO-SLO image.

<<Step S433>>

Subsequently, in step S433, the registration unit 141 performs registration between the overlapped WF-SLO image and the overlapped AO-SLO images of the same set acquired in step S432. Then, the registration unit 141 acquires positional information of the positions of the respective AO-SLO images on the WF-SLO image.

Differently from the inter-frame registration of step S431, herein, registration between the images having different resolutions is required. In this case, since registration is more accurate if the resolutions of the images are mutually close, first, registration of the overlapped WF-SLO image and the L-view-angle overlapped AO-SLO image, which has the lowest resolution, is performed, and positional information of the L-view-angle AO-SLO image corresponding to the WF-SLO image is acquired. Then, a composition image in which the L-view-angle overlapped AO-SLO image is embedded at a corresponding position of the overlapped WF-SLO image is generated.

If a plurality of WF-SLO images are present in the same set, the registration unit 141 determines the WF-SLO image which serves as a reference (hereinafter, referred to "reference WF-SLO image") and performs registration of the L-view-angle overlapped AO-SLO image with respect to the overlapped WF-SLO thereof. Then, the registration unit 141 registers all the L-view-angle overlapped AO-SLO images with respect to the composition image generated in the previous step and updates the composition image by embedding them at the corresponding positions. When the association of the L-view-angle overlapped AO-SLO images is completed, the M-view-angle overlapped AO-SLO images which have the next lowest resolution are processed in a manner similar to that in the case of the view angle L to update the composition image. Then, registration of the S-view-angle overlapped AO-SLO images is also similarly performed.

There are a plurality of methods of registration. However, also in this step S433, as well as step S431, registration is performed by using the phase-only correlation method. However, in order to support registration between the images having different resolutions, all the planar images (the overlapped WF-SLO image and the L-view-angle, M-view-angle, and S-view-angle overlapped AO-SLO images) are adjusted to the resolution of 4.25 µ/pixel, which is the same as that of the view angle L. Specifically, in the case of the M-view-angle and S-view-angle overlapped AO-SLO images, they are downsampled by 2.07 times and 5 times, respectively; and, in the case of the overlapped WF-SLO image, it is upsampled by about 3.5 times. Furthermore, in order to adjust differences in contrast due to the view angles, preprocessing by a low-pass filter or a high-pass filter is performed.

Registration within each of the sets is performed by performing the above processes of steps S431 to S433 with respect to all the sets acquired in step S420, and the process of S430 of FIG. 4 is completed.

Herein, the case that the sets of the planar images are acquired when time-course comparison is to be performed and that registration is performed within each set has been described. However, in practice, in some cases, when each set is acquired, registration between images is performed in order to perform viewing or analysis of images within the same set. In that case, in the state in which the process of step S433 is completed, the information thereof is saved in the database 500; therefore, when the set of the planar images is acquired in step S420, the information of registration performed in step S430 is also acquired at the same time, and the process of step S430 is not performed.

<Step S440>

Subsequently, in step S440, in order to perform registration between the sets of the planar images acquired in step S420, the registration unit 141 performs registration between the reference WF-SLO images of the sets. In this process, the registration unit 141 generates positional information of the registration between the reference WF-SLO images of the sets. The inter-set registration in this step S440 corresponds to second registration.

Herein, the registration unit 141 selects the set which serves as a reference (hereinafter, the selected set will be referred to as "baseline set") from among the sets acquired along the time course with respect to the same subject eye. This baseline set is a set which serves as the reference of time-course comparison, a newest set among the sets of the planar images acquired with respect to the same subject eye is selected in some cases, and an oldest set is selected in some cases. Alternatively, the set may be selected by the user in accordance with the progress of a disease or the like.

The above described registration between the reference WF-SLO images is performed by acquiring the positional relationship of the reference WF-SLO image of each of the planar image set with respect to the reference WF-SLO image included in the baseline set (hereinafter, referred to as "baseline WF-SLO image"). Specifically, the registration unit 141 cuts out a region of 400 pixels×400 pixels from each of the baseline WF-SLO image and the reference WF-SLO image of one set, performs contrast adjustment so that the average-values/dispersions of luminance histograms of the images become the same, and then acquires parallel moving amounts by using the phase-only correlation method. Then, the registration unit 141 performs similar processes with respect to the reference WF-SLO images of all the planar image sets and acquires relative positions (parallel moving amounts) of the sets with respect to the baseline set. Then, the registration unit 141 stores the obtained relative positions of the sets into the storage unit 150 via the control unit 130.

<Step S450>

Subsequently, in step S450, the superimposition unit 142 generates a superimposed image by superimposing all the AO-SLO images on the baseline WF-SLO image based on the results of the registration within the same set (first registration) in step S430 and the results of registration between the sets (second registration) in step S440. Then, the control unit 130 performs control of displaying the superimposed image, which has been generated by the superimposition unit 142, by the display via the output unit 160.

Herein, it is assumed that the superimposed image is generated by using only the images having the view angle(s) serving as targets of photoreceptor-cell analysis. In the present embodiment, since only the view angle S serves as the analysis targets, a case in which a superimposed image using only the view angle S is generated will be described.

First, regarding the S-view-angle AO-SLO images which are included in the baseline set among the sets of the planar images acquired in step S420, the superimposition unit 142 acquires relative-position information of the overlapped AO-SLO images, which have been obtained in step S433, with respect to the baseline WF-SLO image. Herein, in the baseline set, the positional information acquired in step S433 can be used without change since the reference WF-SLO image of step S433 matches the baseline WF-SLO image.

Then, regarding the S-view-angle AO-SLO images included in the sets excluding the baseline set among the sets of the planar images acquired in step S420, the superimposition unit 142 acquires the relative-position information acquired in step S440 and the relative-position information acquired in step S433. Specifically, the superimposition unit 142 acquires the relative-position information of the baseline WF-SLO image and the reference WF-SLO images of the sets in step S440 and acquires the relative-position information of the reference WF-SLO image and the overlapped AO-SLO images in step S443. Then, by using this relative-position information, the superimposition unit 142 acquires the relative-position information of the baseline WF-SLO image and the overlapped AO-SLO images. In the present embodiment, only parallel movement positions are acquired as the relative positions of the baseline WF-SLO image and the reference WF-SLO images of the sets, and parameters of rotations, shear, etc. acquired from affine transformations are not taken into consideration. However, these may be taken into consideration.

Then, based on the positional information of all the S-view-angle overlapped AO-SLO images serving as targets with respect to the baseline WF-SLO image, the superimposition unit 142 generates a superimposed image in which, for example, pixel values are changed by reflecting the quantity of the number of overlapped images. Specifically, when the superimposed image is to be generated, first, the superimposition unit 142 obtains, from the positional information of the S-view-angle overlapped AO-SLO images, regions in which the images are present on the baseline WF-SLO image and, with respect to each pixel, acquires the number of the AO-SLO images superimposed thereon. Then, the luminance values of the baseline WF-SLO image are converted to those for display. There are a plurality of methods of the conversion; however, in this case, a highest luminance value and a lowest luminance value of the baseline WF-SLO image are acquired, the difference therebetween is divided by 255, and the depth of pixels is 8 bits. If such a conversion is performed, the lowest luminance value of the baseline WF-SLO image becomes 0, and the highest luminance value thereof becomes 255. Then, if the pixel value is 0 (no AO-SLO image to be overlapped), the superimposition unit 142 sets the converted luminance value of the corresponding pixel of the baseline WF-SLO image; and, if the pixel value is other than 0, the superimposition unit 142 sets the luminance value to which the number of superimposition is reflected. For example, if the number of the S-view-angle overlapped AO-SLO images present at a certain pixel is M in a case in which the number of all the S-view-angle overlapped AO-SLO images is N, the luminance value I thereof is set in a manner of Expression (1).

[Mathematical Expression 1]

$$I = depth * \frac{M}{N} \quad (1)$$

Herein, various methods are conceivable as the way to determine the value of "I". For example, instead of the number of all the S-view-angle overlapped AO-SLO images, N may be the highest value of the number of the AO-SLO images to be superimposed on the pixel. Alternatively, there is also a conceivable method in which N is the number determined in advance (for example, 30), and, if M is larger than N, I is depth.

Figure 6:
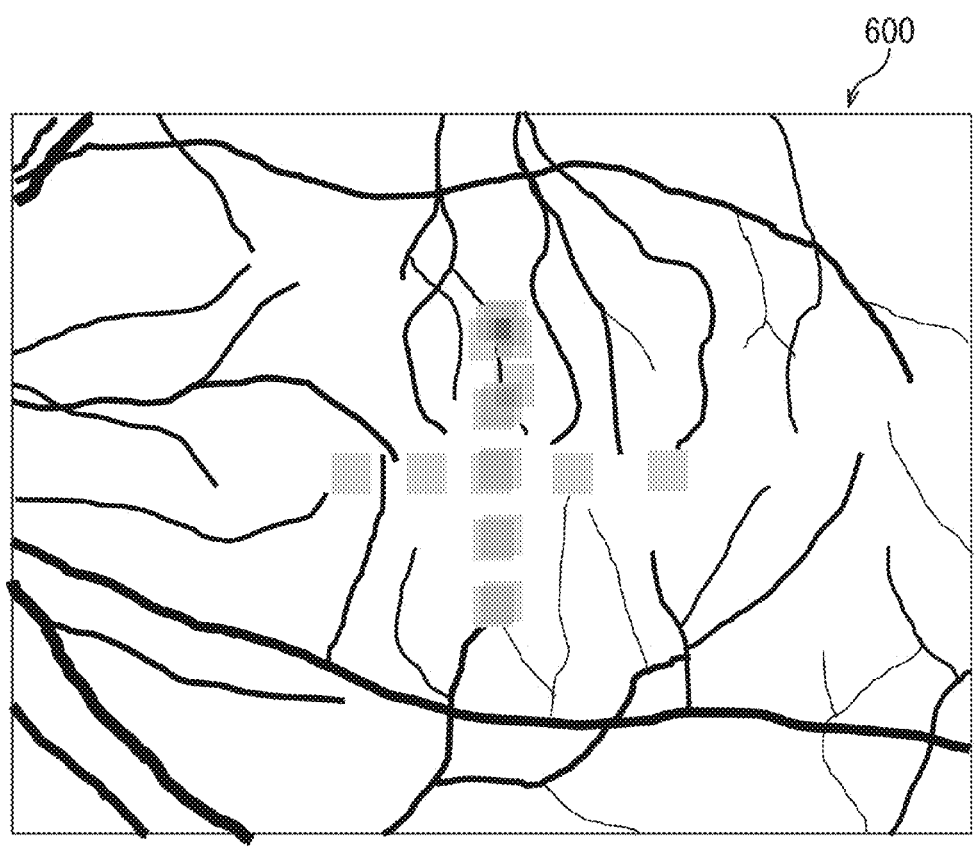
FIG. 6 is a view, according to the first embodiment of the present disclosure, schematically showing an example of a superimposed image generated in step S450 of FIG. 4.

FIG. 6 is a view, according to the first embodiment of the present disclosure, schematically showing an example of a superimposed image 600 generated in step S450 of FIG. 4. In the superimposed image 600 shown in FIG. 6, an example in which only the number of overlapped AO-SLO images is reflected by gray scale is shown. However, various methods are conceivable other than this method. For example, the volume of the number of the overlapped AO-SLO images can be shown by colors. Furthermore, for example, the superimposed image can be also generated with different colors respectively for the sets in which the overlapped AO-SLO images are included.

Then, the control unit 130 performs control to store the superimposed image, which has been generated by the superimposition unit 142, into the storage unit 150 and performs control to display the superimposed image by the external display 400 through the output unit 160.

<Step S460>

Subsequently, in step S460, the information acquiring unit 120 performs a process of acquiring an evaluation region selected by the user from the information input device 300. Then, the information acquiring unit 120 stores the acquired evaluation region into the storage unit 150 via the control unit 130. Herein, the evaluation region is, for example, a region selected as a region which is to be subjected to time-course evaluation by using a mouse or the like by a user on the superimposed image displayed by the display 400 in step S450. More specifically, coordinates thereof can be acquired when the user clicks one point on the superimposed image displayed by the display 400, or a region can be specified and selected on the superimposed image. Furthermore, without depending on input by the user, an evaluation region can be also acquired automatically from the superimposed image. For example, the information acquiring unit 120 can acquire a region in which the number of superimposed images is the largest on the superimposed image as an evaluation region or can acquire a region in which the number of superimposed images belonging to different planar-image sets is the largest as an evaluation region. Furthermore, when the number of images is to be counted in such a manner, the information acquiring unit 120 can give weights by image quality such as contrasts of the images and acquire a region in which the number of the images having image quality higher than a predetermined threshold value as an evaluation region.

<Step S470>

Subsequently, in step S470, from among all the S-view-angle overlapped AO-SLO images generated in step S432, the image selecting unit 143 selects the overlapped AO-SLO images that include the evaluation region acquired in step S460. Then, the control unit 130 performs control to display a list of the overlapped AO-SLO images, which have been selected by the image selecting unit 143, by the external display 400 through the output unit 160.

Furthermore, from among the overlapped AO-SLO images including the evaluation region acquired in step S460, the image selecting unit 143 selects the images to be subjected to fine registration for time-course analysis (hereinafter, referred to as "analysis-target AO-SLO images"). In this selection, the images can be selected by the user, or the images can be also selected automatically by the image selecting unit 143 according to an algorithm. For example, the case in which the user is to select the images employs a mode in which the user selects the analysis-target AO-SLO images in consideration of an image-taken date, image quality, etc. from among the list of all the overlapped AO-SLO images including the displayed evaluation region. Meanwhile, the case in which the image selecting unit 143 is to perform automatic selection employs a mode in which the image having the highest image quality is selected for each image-taken date, or the image including, at a position closer to the center thereof, the evaluation region acquired in step S460 is selected as a reference image for each image-taken date. Then, the image selecting unit 143 stores the selected analysis-target AO-SLO images into the storage unit 150 via the control unit 130.

<Step S480>

Subsequently, in step S480, the registration unit 141 performs fine registration between the analysis-target AO-SLO images selected in step S470. In this process, the registration unit 141 generates positional information of the registration between the analysis-target AO-SLO images. This fine registration in step S480 corresponds to third registration.

Herein, as a method of the fine registration, a case in which the phase-only correlation method similar to that of the registration within the set in step S430 is used will be described. However, there are a plurality of methods for the registration, and the method is not limited to this method.

Specifically, in step S480, first, the registration unit 141 selects an image which serves as a reference (hereinafter, referred to as "reference AO-SLO image") from among the analysis-target AO-SLO images. This selection of the reference AO-SLO image may be configured to select the image depending on a target to be observed by the user or may be configured to automatically select the image by software. As a specific example of the automatic selection, the image having image quality higher than a predetermined threshold value, for example, having a high contrast is selected, and the image which includes the evaluation region, which has been acquired in step S460, at a position closer to the center thereof.

Then, the registration unit 141 registers the images which are included in the analysis-target AO-SLO images and are not the reference AO-SLO image with the reference AO-SLO image. Herein, a method similar to that of the inter-frame registration of step S431 is used, and preprocessing for image adjustment between the analysis-target AO-SLO images is performed. A reason therefor is due to a characteristic that the image quality of the analysis-target AO-SLO images is varied since these are overlapped images acquired along a time course while, in the case of the inter-frame registration, the properties of the images are similar since it is the registration among the 32 frames acquired in one second.

As the preprocessing herein, contrast adjustment by LOG often used in photoreceptor cell observations is performed. More specifically, a histogram of luminance of each image is obtained, and a highest value and a lowest value of luminance with the luminance value of upper/lower 0.5% thereof cut are assumed to be "Imax" and "Imin", respectively. Then, in the contrast adjustment LOG, a luminance value I of each pixel is changed in the manner of following Expression (2).

[Mathematical Expression 2]

$$I_{processed} = I_{norm} \log \frac{(I - I_{min} + a)}{a} \quad (2)$$

$$I_{norm} = \frac{I_{depth}}{\log \frac{(I_{max} - I_{min} + a)}{a}} \quad (3)$$

Herein, "Iprocessed" shown in Expression (2) is a pixel value after the adjustment. Meanwhile, "Inorm" shown in Expression (2) is a constant for normalization so that the highest value of luminance becomes a highest value allowed by the pixel depth (for example, 16 bits or 8 bits), and "Inorm" is as shown by Expression (3). Also, "a" shown in Expression (2) and Expression (3) is a parameter used in the contrast adjustment by LOG; wherein, the smaller the value, the larger the adjustment. In the present embodiment, 5000 is selected from a range of 100 to 5000 suitable as the range of "a".

After the preprocessing like this is performed, the registration unit 141 performs registration by a method similar to that of step S431 to generate registered analysis-target AO-SLO images with respect to the analysis-target AO-SLO images. Moreover, if the fine registration does not go well (for example, if a correlation peak of phase-only correlation is equal to or less than a threshold value), the registration unit 141 acquires the information that at which stage it failed as error flag information. Then, the registration unit 141 stores the registered analysis-target AO-SLO images generated in this manner and the information of registration results into the storage unit 150 via the control unit 130.

<Step S490-1>

Subsequently, in step S490-1, the region extracting unit 144 extracts a common region which is a region included in common in the registered analysis-target AO-SLO images obtained as a result of the fine registration in step S480.

<Step S490-2>

Subsequently, in step S490-2, the control unit 130 performs control to display, by the display 400, the common region extracted in step S490-2 together with the registered analysis-target AO-SLO images and the information of the registration results thereof obtained in step S480.

Figure 7:
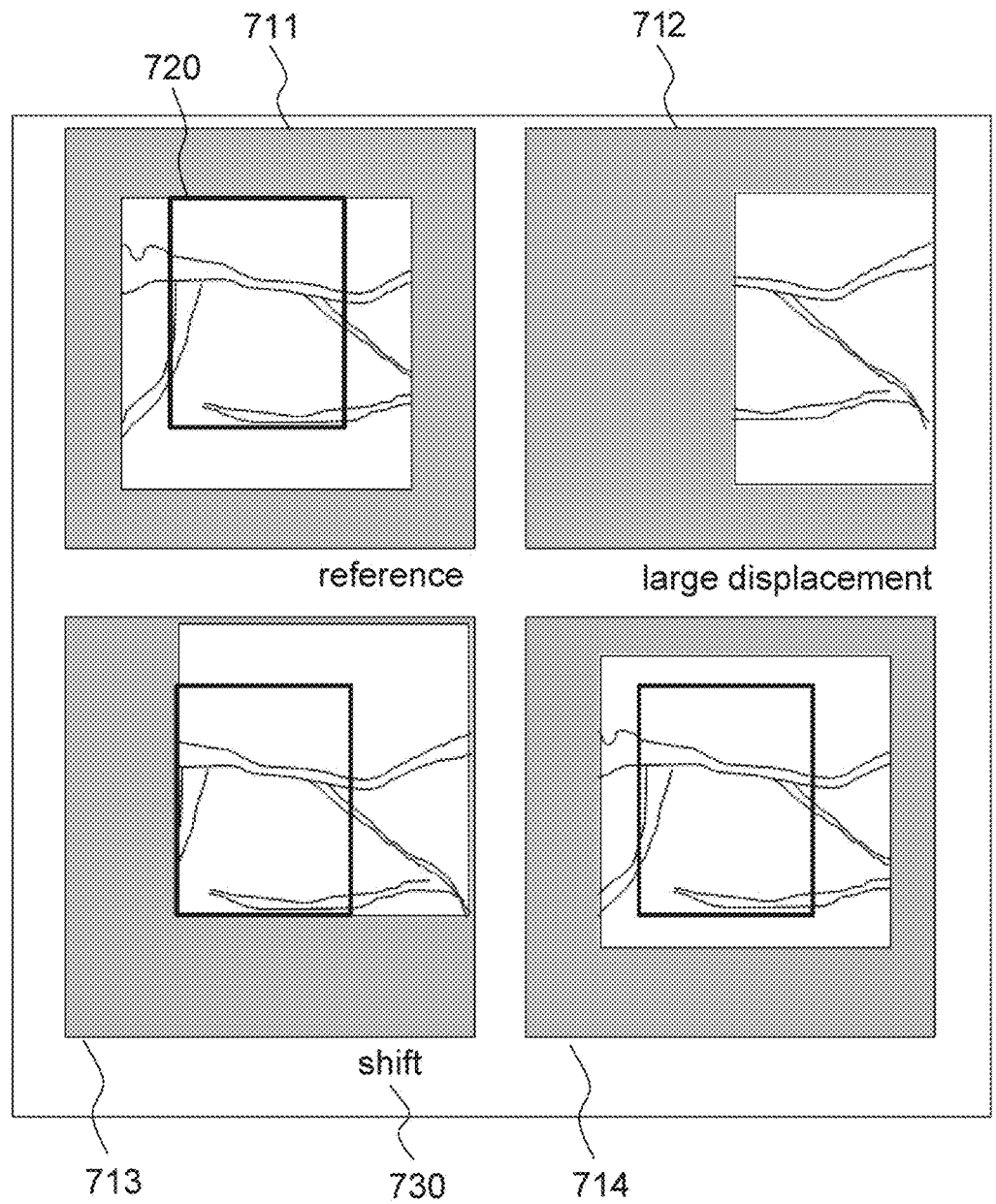
FIG. 7 is a view, according to the first embodiment of the present disclosure, schematically showing a display example of registered time-course-analysis-target AO-SLO images, etc.

FIG. 7 is a view, according to the first embodiment of the present disclosure, schematically showing a display example of the registered analysis-target AO-SLO images, etc. In this FIG. 7, registered analysis-target AO-SLO images 711 to 714 are shown in juxtaposition, and, at the same time, a common region 720 is shown.

Furthermore, a region 730 showing error flag information, etc. acquired in the stage of the fine registration is added to each image. Specifically, FIG. 7 shows an example describing a case in which the image is a reference AO-SLO image (displayed as "reference") and a case in which the moving amount is large with respect to the reference AO-SLO image although fine registration has been performed (displayed as "large displacement").

Herein, the case of the image having the large moving amount is excluded from the analysis targets for a reason that, if such an image is included, the size of the common region 720 becomes extremely small. In the present embodiment, if the center position of an image is distant from the center of the reference AO-SLO image by 40% or more, the image is excluded from the analysis targets. Meanwhile, in the error flag information acquired in step S480, display that represents only parallel movement (displayed as "shift") is performed in a case of the image in which the process proceeds to the parallel movement of the entire image but has an error in a distortion correction part such as affine transformation thereafter. This represents that this image is roughly at a right position, but has not been registered at the level of each one of photoreceptor cells, and is not at the level for judging whether individual photoreceptor cells have been recovered or lost or not, although it is available for, for example, comparison of the photoreceptor-cell density in a selected region.

The control unit 130 performs control to store the registered analysis-target AO-SLO images obtained in this manner, the information of the registration results thereof, and the common region 720 into the storage unit 150 and performs control to display them by the external display 400 through the output unit 160. Furthermore, the output unit 160 outputs and saves the acquired information, etc. to/in the database 500. Note that, although it is not illustrated, in the vicinity of each of the displayed AO-SLO images, the information of the image-taken date, etc. of each of them is displayed together.

When the process of step S490 is completed, the process of the flow chart shown in FIG. 4 is completed.

In the image processing device 100 according to the first embodiment, the AO-SLO images acquired along the time course are mutually registered and superimposed on the WF-SLO image, which is a reference, so that a superimposed image is generated.

According to such a configuration, for example a region in which the AO-SLO images are repeatedly taken along the time course can be understood, time-course comparison at the eye fundus of the subject eye can be efficiently performed. Furthermore, for example, time-course comparison of many images can be performed by selecting images from the periphery of the region in which AO-SLO images are repeatedly taken and performing fine registration.

(Second Embodiment)

Next, a second embodiment of the present disclosure will be described.

In the first embodiment, the method of mutually registering the AO-SLO images acquired along the time course, superimposing them on the WF-SLO image which is the reference, generating and displaying the superimposed image, and, based on the superimposed image, acquiring the region in which the number of taken images is large as the evaluation region has been described. Furthermore, in the first embodiment, the method of selecting the AO-SLO images including the evaluation region from among the AO-SLO images, performing fine registration thereof, and extracting and displaying the actually overlapped common region has been also described.

In the second embodiment, with respect to the time-course analysis-target AO-SLO images which have undergone fine registration of step S480 in the first embodiment, a method of extracting the common region of each image and performing analysis such as evaluation of periodic structures and photoreceptor-cell detection will be described.

Since a schematic configuration of an ophthalmic apparatus according to the second embodiment is similar to the schematic configuration of the ophthalmic apparatus 10 according to the first embodiment shown in FIG. 1, the description thereof is omitted.

[Processing Procedure of the Image Processing Device 100]

Figure 8:
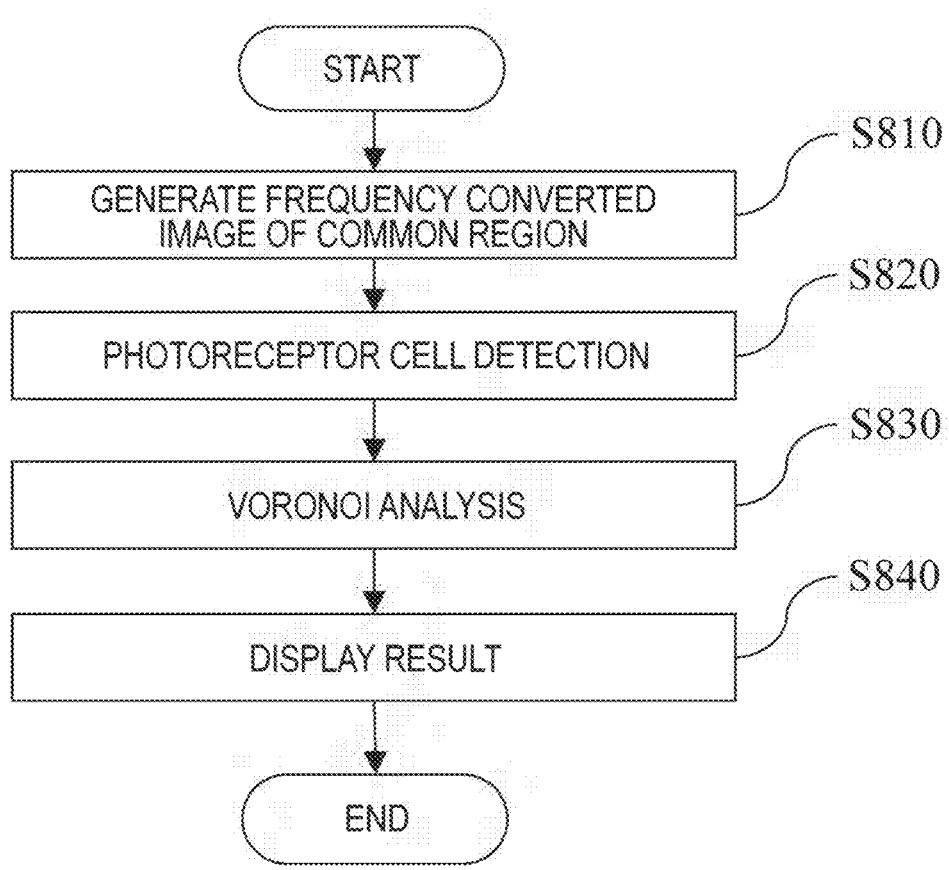
FIG. 8 is a flow chart showing an example of a processing procedure of an image processing method by an image processing device according to a second embodiment of the present disclosure.

FIG. 8 is a flow chart showing an example of a processing procedure of an image processing method by the image processing device 100 according to the second embodiment of the present disclosure. Herein, it is assumed that, in the stage of "START" of the flow chart shown in FIG. 8, the processes of steps S410 to S490-1 shown in FIG. 4 have been completed.

<Step S810>

After the processes of steps S410 to S490-1 shown in FIG. 4 are performed, in step S810, first, the analysis unit 145 acquires the registered time-course analysis-target AO-SLO images obtained in step S480 and the information of the common regions extracted in step S490-1 from the database 500. Then, from each registered analysis-target AO-SLO image, the analysis unit 145 generates a spatial-frequency transformation image of a region extracted as the common region.

Specifically, first, a square image region having a width and height larger than those of the common region and having an integer of 2 to the power of N as an image size is set, and the above described extracted region is placed at the center thereof. This is referred to as spatial-frequency transforming extracted image, and, in this case, the size thereof is 512 pixels×512 pixels. Herein, an average value of all the pixel values of the common region is obtained, the average value is subtracted from each pixel value of the common region, and the pixel value not corresponding to the common region is set to 0. Furthermore, in order to prevent influence by discontinuity at a boundary part of the common region, a process by a window function is performed. In this case, a Hann window having a size of 8 pixels is used. Each of the frequency-transforming extracted images generated in this manner is subjected to FFT processing (fast Fourier transformation) to generate a power spectral image, wherein each pixel value is the magnitude of the amplitude of FFT. Herein, the power spectral image is known to have a ring-shaped structure to which periods of photoreceptor cells are reflected. Therefore, the radius of the ring is obtained from the power spectral image, and the period of photoreceptor cells is roughly estimated from the power spectral image. There are a plurality of methods to obtain the radius of the ring. However, in this case, the image center of the power spectral image is used as an original point, the pixel values of the power spectral image are accumulated in an angular direction, and a location at which the accumulated value is the largest in a moving-radius direction is used as the radius of the ring.

The value of each pixel value of the power spectral image is representing the degree of intensity at which the periodic structure of the photoreceptor cells in the corresponding direction is present. However, in this case, particular directions are not taken into consideration regarding the distribution of the photoreceptor cells. Therefore, the angle components about the direction are accumulated, and only the size of the periodic structure is focused on. If the ring radius on the power spectral image obtained by the above described method is "r", an inter-photoreceptor-cell distance L in this case can be estimated in a manner shown by following Expression (4).

[Mathematical Expression 3]

$$L = \frac{\text{image\_size} * \text{pixel\_size}}{r} = \frac{512 * 0.85}{r} \quad (4)$$

Herein, the size of the power spectral image (image_size) is 512 pixels×512 pixels as described above, and the size of a pixel (pixel_size) is 0.85 μ/pixel in the case of the S-view-angle AO-SLO image.

If the common regions of all the registered analysis-target AO-SLO images are the same images, the inter-photoreceptor-cell distance L is the same in all the power spectral images. However, in practice, the value of the inter-photoreceptor-cell distance L is different in each image. This can be categorized into: a case in which clinical changes such as changes in the photoreceptor cell density due to progress of a disease have been correctly reflected; a case in which equal regions are not selected due to failure of registration; and a case in which right images have not been acquired due to deterioration in image quality or misalignment of focus positions. However, it is known that, even in a case in which photoreceptor cells are lost due to the progress of a disease, in many cases, the photoreceptor cells are not disposed again so as to uniformly increase the inter-photoreceptor-cell distance L, but only the affected photoreceptor cells are lost, and large changes are not observed at the other photoreceptor cells. Therefore, in many cases, the images in which the value of the inter-photoreceptor-cell distance L is largely changed are indicating some problems (registration failure, failure in image taking, etc.). Therefore, the validity of the analysis results can be presented to the user by presenting, for example, the value of the inter-photoreceptor-cell distance L or an index calculated by using the value of the inter-photoreceptor-cell distance L.

Then, the control unit 130 performs control to store the information of the inter-photoreceptor-cell distance L of the common region acquired by the analysis unit 145 in this manner into the storage unit 150 and performs control to display that by the external display 400 through the output unit 160. At the same time, the output unit 160 outputs and saves the information of the inter-photoreceptor-cell distance L to and in the database 500. Herein, a plurality of ways are conceivable as the way to present the inter-photoreceptor-cell distance L or the index based on the inter-photoreceptor-cell distance L to the user. However, for example, presenting or the like to the comment region of FIG. 7 (730 of FIG. 7) is appropriate.

<Step S820>

Subsequently, in step S820, the analysis unit 145 performs photoreceptor-cell detection based on the inter-photoreceptor-cell distance corresponding to the reference AO-SLO image among the inter-photoreceptor-cell distances L corresponding to the common regions of the registered time-course analysis-target AO-SLO images acquired in step S810. Herein, a plurality of methods are known as the method of the photoreceptor-cell detection, and, for example, a method of detecting a local highest value of the luminance values of an image is known. In this method, two points detected in the distance shorter than the size corresponding to the inter-photoreceptor-cell distance are united by a fusing process. It is conceivable to use the inter-photoreceptor-cell distance L as a parameter in this process. However, if all of the two points in the distance equal to or less than the inter-photoreceptor-cell distance L are fused, almost all of detection points are fused since there are fluctuations in the distribution of photoreceptor cells. Therefore, in the present embodiment, the two points equal to or less than 0.6 L are fused. Then, the control unit 130 performs control to store, into the storage unit 150, the coordinate information of the detection points detected in the common regions of the registered analysis-target AO-SLO images acquired in this manner by the analysis unit 145.

<Step S830>

Subsequently, in step S830, based on the coordinate information of the detection points acquired in step S820, the analysis unit 145 performs voronoi analysis, etc. and extracts an index about the distribution of the photoreceptor cells. Then, the control unit 130 performs control to store, into the storage unit 150, the index information of the distribution of the photoreceptor cells acquired in this manner by the analysis unit 145.

<Step S840>

Subsequently, in step S840, the control unit 130 performs control to display the detection results of the photoreceptor cells acquired in step S820 and the analysis results acquired in step S830 by the external display 400 through the output unit 160. In this process, the control unit 130 performs control to display them by comparison so that differences in the time-course analysis results can be compared among the common regions of the registered analysis-target AO-SLO images.

Herein, as the comparison display of the analysis results, the comparison results of the entire common region can be displayed, or the comparison display can be performed only in a selected region selected within the common region by the user. Specifically, the time-course changes of the index such as the photoreceptor-cell density or the hexagon rate of voronoi calculated in the selected region can be displayed by comparison for the user by a list, a graph, or the like. Moreover, whether or not the detection points in the selected region match the detection points in the images acquired on different date can be shown by changing the colors of displayed detection points.

Furthermore, display can be changed by comparing the indexes acquired as a result of the voronoi analysis. For example, comparison display can be performed with the colors of the detection points and the colors of voronoi regions changed depending on the change rate of the values of nearest neighbor distances (NND: Nearest Neighbor Distances), or comparison display can be performed depending on changes in the difference of the areas of voronoi regions, difference in the number of apexes, and difference in the index representing a shape such as an eccentricity rate. Moreover, instead of contour-line display of the density, differences in the density or differences in the hexagon rate or the like of the voronoi region can be subjected to contour line display. In this case, regions having small changes and regions having large changes are clearly shown so that in which region a disease is progressing can be intuitively understood.

When the process of step S840 is completed, the process of the flow chart shown in FIG. 8 is completed.

According to the second embodiment in addition to the effects of the above described first embodiment, following effects are exerted. Specifically, when the states of the progress of a disease, etc. are desired to be compared by using the images acquired along a time course, analysis indexes reflecting the states of photoreceptor cells can be acquired and compared among the same finely registered image-taken regions, and the comparison results thereof can be displayed as a list.

Other Embodiments

Embodiment(s) of the present disclosure can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present disclosure has been described with reference to exemplary embodiments, it is to be understood that the disclosure is not limited to the disclosed exemplary embodiments. The scope of the following claims is to be accorded the broadest interpretation so as to encompass all such modifications and equivalent structures and functions.

This application claims the benefit of Japanese Patent Application No. 2015-241565, filed Dec. 10, 2015, which is hereby incorporated by reference herein in its entirety.

What is claimed is:

1. An image processing device comprising:
   an image acquirer configured to acquire first images and second images included in a first and a second sets, wherein each of the first and the second sets includes at least one of the first images obtained by imaging a first region having a predetermined size at an eye fundus of a subject eye and the second images obtained by imaging a second region smaller than the predetermined size, and
   wherein the first and the second images included in a same set are associated with each other based on an imaging period;
   a registerer configured to perform
   first registration of the first image and the second images included in the same set and
   second registration of the first images included in different sets and
   to generate positional information of the first registration and the second registration; and
   a superimposer configured to superimpose
   the second images included in the first set and the second images included in the second set acquired after the first set on one of the first images included in the first set or one of the first images included in the second set based on the positional information generated by the registerer to generate a superimposed image;
   a region acquirer configured to acquire, from within the superimposed image, an evaluation region serving as a partial region subject to time-course evaluation;
   an image selector configured to select the second images subject to fine registration from among the second images including the evaluation region;
   a region extractor configured to extract a common region included in common in the second images subject to a third registration, the third registration being fine registration of the second images selected by the image selector and being performed by the registerer; and
   a controller configured to perform control to display the common region and a result of the third registration.

2. The image processing device according to claim 1, wherein
   the image acquirer acquires the second images for each of the first and the second sets; and
   the superimposed image has a pixel value corresponding to a number of overlap of the second images included in the first set and the second images included in the second set.

3. The image processing device according to claim 1, wherein
   the image acquirer acquires the second images for each of the first and the second sets; and
   the superimposed image has a pixel value corresponding to a number of overlap of the second images included in the first set and a number of overlap of the second images included in the second set.

4. The image processing device according to claim 1, wherein:
   the controller is further configured to perform control to display the common region and the result of the third registration by a display together with the second images subject to the third registration.

5. The image processing device according to claim 4, wherein the region acquirer acquires, as the evaluation region, a region having a largest number of overlap of the second images in the superimposed image.

6. The image processing device according to claim 4, wherein the region acquirer acquires, as the evaluation region, a region that has a largest number of overlapping of the second images included in the first and the second sets in the superimposed image.

7. The image processing device according to claim 4, wherein the region acquirer acquires, as the evaluation region, a region that has a largest number of overlapping of the second images in consideration of image quality in the superimposed image.

8. The image processing device according to claim 4, wherein, when the third registration is to be performed, the registerer selects, as a reference image, the second image including the evaluation region at a position closer to a center thereof from among the second images selected by the image selector.

9. The image processing device according to claim 1, further comprising:
   a region acquirer configured to acquire, from within the superimposed image, an evaluation region serving as a partial region to be subjected to time-course evaluation;
   an image selector configured to select the second images to be subjected to fine registration from among the second images including the evaluation region;
   an extractor configured to extract a common region that is a region included in common in the second images subjected to a third registration, the third registration being fine registration of the second images selected by the image selector and being performed by the registerer;
   an analyzer configured to analyze a photoreceptor cell of the subject eye in the common region; and
   a controller configured to perform control of displaying a result of analysis by the analyzer on a display.

10. The image processing device according to claim 9, wherein, when the photoreceptor cell is to be analyzed,
    the analyzer acquires an index based on a periodic structure of the photoreceptor cell about the common region and
    analyzes detection of the photoreceptor cell and distribution of the photoreceptor cell based on the index.

11. The image processing device according to claim 9, wherein the controller performs to display, on the display, results of the analysis by the analyzer in a mode that the results can be compared in the common region between the second images subjected to the third registration.

12. The image processing device according to claim 11, wherein the controller performs control to display a difference in detection results of the photoreceptor cell by the analyzer in the comparable mode.

13. The image processing device according to claim 11, wherein
    the analyzer analyzes distribution of the photoreceptor cell by using voronoi analysis; and
    the controller performs control to display a difference in a result of the voronoi analysis in the comparable mode.

14. The image processing device according to claim 13, wherein the difference in the result of the voronoi analysis is at least any of: a difference in a nearest neighbor distance at each detection point by the voronoi analysis; a difference in the number of vertexes of a voronoi region by the voronoi analysis; a difference in an area of the voronoi region; and a difference in a shape of the voronoi region.

15. The image processing device according to claim 11, wherein the controller performs control to display a difference in density or a difference in a hexagon rate caused by the analyzer in the comparable mode by displaying the difference by a contour line by the display.

16. An image processing method comprising:
an image acquiring step of acquiring first images and second images included in a first and a second sets, wherein each of the first and second sets includes
at least one of the first images obtained by imaging a first region having a predetermined size at an eye fundus of a subject eye and
the second images obtained by imaging a second region smaller than the predetermined size, and
wherein the first and second images including a same set are associated with each other based on an imaging period;
a registering step of performing
first registration of the first image and the second image included in the same set and
second registration of the first images included in different sets and
to generate positional information of the first registration and the second registration;
a superimposing step of superimposing
the second image included in the first set and the second images included in the second set acquired after the first set on
one of the first images included in the first set or one of the first images included in the second set based on the positional information generated in the registering step to generate a superimposed image;
acquiring, from within the superimposed image, an evaluation region serving as a partial region subject to time-course evaluation;
selecting the second images subject to fine registration from among the second images including the evaluation region;
extracting a common region included in common in the second images subject to a third registration, the third registration being fine registration of the selected second images; and
performing control to display the common region and a result of the third registration.

17. A non-transitory storage medium including a program, when executed, causing a computer to execute the steps of the image processing method comprising:
an image acquiring step of acquiring first images and second images included in a first and a second sets, wherein each of the first and the second sets includes
at least one of the first images obtained by imaging a first region having a predetermined size at an eye fundus of a subject eye and
the second images obtained by imaging a second region smaller than the predetermined size, and
wherein the first and second images including a same set are associated with each other based on an imaging period;
a registering step of performing
first registration of the first image and the second images included in the same set and
second registration of the first images included in different sets and
to generate positional information of the first registration and the second registration;
a superimposing step of superimposing
the second images included in the first set and the second images included in the second set acquired after the first set on
one of the first images included in the first set or one of the first images included in the second set based on the positional information generated in the registering step to generate a superimposed image
acquiring, from within the superimposed image, an evaluation region serving as a partial region subject to time-course evaluation;
selecting the second images subject to fine registration from among the second images including the evaluation region;
extracting a common region included in common in the second images subject to a third registration, the third registration being fine registration of the selected second images; and
performing control to display the common region and a result of the third registration.

* * * * *